US011185526B2

(12) United States Patent
Ghalili et al.

(10) Patent No.: US 11,185,526 B2
(45) Date of Patent: *Nov. 30, 2021

(54) CANNABINOID, MENTHOL AND CAFFEINE DISSOLVABLE FILM COMPOSITIONS, DEVICES AND METHODS

(71) Applicants: Babak Ghalili, New York, NY (US); Emma Ghalili, New York, NY (US)

(72) Inventors: Babak Ghalili, New York, NY (US); Emma Ghalili, New York, NY (US)

( * ) Notice: Subject to any disclaimer, the term of this patent is extended or adjusted under 35 U.S.C. 154(b) by 40 days.

This patent is subject to a terminal disclaimer.

(21) Appl. No.: 16/558,872

(22) Filed: Sep. 3, 2019

(65) Prior Publication Data

US 2020/0069639 A1  Mar. 5, 2020

Related U.S. Application Data

(63) Continuation-in-part of application No. 16/419,336, filed on May 22, 2019, now Pat. No. 10,751,299.

(60) Provisional application No. 62/726,713, filed on Sep. 4, 2018.

(51) Int. Cl.
| | | |
|---|---|---|
| *A61K 9/70* | (2006.01) | |
| *A61K 31/353* | (2006.01) | |
| *A61K 9/00* | (2006.01) | |
| *A61K 31/522* | (2006.01) | |
| *A61K 31/05* | (2006.01) | |
| *A61K 36/185* | (2006.01) | |
| *A61K 31/465* | (2006.01) | |
| *A61K 31/197* | (2006.01) | |
| *A61K 31/675* | (2006.01) | |
| *A61K 31/4188* | (2006.01) | |
| *A61K 31/525* | (2006.01) | |

(52) U.S. Cl.
CPC .......... *A61K 31/353* (2013.01); *A61K 9/0056* (2013.01); *A61K 9/7007* (2013.01); *A61K 31/05* (2013.01); *A61K 31/197* (2013.01); *A61K 31/4188* (2013.01); *A61K 31/465* (2013.01); *A61K 31/522* (2013.01); *A61K 31/525* (2013.01); *A61K 31/675* (2013.01); *A61K 36/185* (2013.01)

(58) Field of Classification Search
CPC .. A61K 31/353; A61K 9/7007; A61K 9/0056; A61K 31/05; A61K 31/522; A61K 31/197; A61K 47/26; A61K 47/46
See application file for complete search history.

(56) References Cited

U.S. PATENT DOCUMENTS

| | | | | |
|---|---|---|---|---|
| 5,192,802 A ‡ | 3/1993 | Rencher | ................ | A61K 9/006 106/35 |
| 5,234,957 A ‡ | 8/1993 | Mantelle | ................ | A61K 9/006 514/77 |
| 7,025,992 B2 ‡ | 4/2006 | Whittle | ................ | A61K 9/0031 424/43 |
| 8,642,645 B2 ‡ | 2/2014 | Kelly | ................ | A61K 36/898 514/45 |
| 9,095,563 B2 ‡ | 8/2015 | Sekura | ................ | A61K 36/00 |
| 9,839,693 B2 ‡ | 12/2017 | Borja | ................ | A61Q 19/00 |
| 10,028,904 B2 ‡ | 7/2018 | Smith | ................ | A61K 31/352 |
| 10,058,531 B1 ‡ | 8/2018 | Chistov | ................ | A61K 31/353 |
| 10,080,736 B2 ‡ | 9/2018 | Kleidon | ................ | A23L 33/115 |
| 10,751,299 B2 * | 8/2020 | Ghalili | ................ | A61K 47/12 |
| 10,813,889 B2 * | 10/2020 | Ghalili | ................ | A61P 25/00 |
| 2008/0112895 A1 ‡ | 5/2008 | Kottayil | ................ | A61K 9/08 424/46 |
| 2009/0036523 A1 | 2/2009 | Stinchcomb et al. | | |
| 2011/0207817 A1 * | 8/2011 | Wetterer | ................ | A61P 1/02 514/544 |
| 2013/0005831 A1 ‡ | 1/2013 | Rajewski | ................ | A61K 9/0056 514/772.2 |
| 2013/0052234 A1 * | 2/2013 | Goldberg | ................ | A61K 31/4045 424/400 |
| 2013/0281523 A1 ‡ | 10/2013 | Letendre | ................ | A61K 9/1611 514/454 |
| 2015/0038594 A1 * | 2/2015 | Borges | ................ | A61K 9/0053 514/772.2 |
| 2016/0051510 A1 | 2/2016 | Allen et al. | | |
| 2016/0166498 A1 ‡ | 6/2016 | Anastassov | ................ | A61K 8/19 424/52 |
| 2016/0228409 A1 | 8/2016 | Cross, III | | |
| 2016/0279073 A1 | 9/2016 | Donsky et al. | | |
| 2017/0021029 A1 ‡ | 1/2017 | Raber | ................ | A61K 47/44 |
| 2017/0112161 A1 | 4/2017 | Bhairam | | |
| 2017/0112823 A1 | 4/2017 | Nigam | | |
| 2017/0239359 A1 ‡ | 8/2017 | Borja | ................ | A23L 29/262 |
| 2017/0252300 A1 | 9/2017 | Modi | | |

(Continued)

FOREIGN PATENT DOCUMENTS

| | | | | | |
|---|---|---|---|---|---|
| WO | WO-2015067422 A1 ‡ | 5/2015 | ............... | A61K 8/19 |
| WO | WO-2017059088 A1 ‡ | 4/2017 | ........... | A61K 31/618 |

OTHER PUBLICATIONS

Iscan, Gokalp, et al., "Antimicrobial Screening of Mentha piperita Essential Oils", Journal of Agricultural and Food Chemistry, vol. 50, Issue 14, May 30, 2002, pp. 3943-3946.‡

"Glycerin", Glycerin Anhydrous, Ophthalgan, Retrieved on Jul. 8, 2019, 2 pages. Available at: www.robholland.com/Nursing/Drug_Guide/data/monographframes/G019.html.‡

Abualhasan, Murad N., et al., "GC Method Validation for the Analysis of Menthol in Suppository Pharmaceutical Dosage Form", International Journal of Analytical Chemistry, vol. 2017, Mar. 6, 2017, 4 pages.‡

"What Does Full Spectrum Mean?" Extract Labs, Jul. 31, 2019, retrieved on Dec. 30, 2019 from the internet https://www.extractlabs.com/cbd-guides/what-does-full-spectrum-mean/, 6 pages.‡

(Continued)

*Primary Examiner* — Mina Haghighatian

(74) *Attorney, Agent, or Firm* — Ziegler IP Law Group, LLC

(57) ABSTRACT

The present disclosure relates to a dissolvable thin oral tape, film or strip or segment thereof composition or device, including a film former, at least one cannabinoid, menthol, caffeine and vitamins.

18 Claims, 7 Drawing Sheets

(56) References Cited

U.S. PATENT DOCUMENTS

| | | | | |
|---|---|---|---|---|
| 2017/0266153 | A1‡ | 9/2017 | Levy | A61K 31/353 |
| 2017/0290870 | A1‡ | 10/2017 | Schaneville | A61K 47/10 |
| 2017/0368020 | A1‡ | 12/2017 | Estey | A61K 9/0058 |
| 2018/0344688 | A1* | 12/2018 | Chistov | A61K 9/006 |
| 2019/0110981 | A1* | 4/2019 | Weimann | A61K 9/7053 |
| 2019/0247299 | A1* | 8/2019 | Cameron | A61K 36/28 |
| 2020/0316151 | A1* | 10/2020 | Ghalili | A61K 31/675 |

OTHER PUBLICATIONS

The International Search Report and Written Opinion of the Searching Authority, Application No. PCT/US2019/048691, dated Jan. 17, 2020, 20 pages.‡

U.S. Appl. No. 16/419,392, filed May 2019.‡

U.S. Appl. No. 16/419,274, filed May 2019.‡

Notification of Transmittal of The International Search Report and The Written Opinion of The International Searching Authority, or The Declaration, Application No. PCT/US19/49309, dated Jan. 27, 2020, 19 Pages.

Wikipedia Article "Cannabinoid"; published online Aug. 30, 2018. 23 Pages.

Echo "What is Full-Spectrum Hemp Oil and Hwy is is Important" Downloaded Apr. 24, 2020, Date May 5, 2017, 5 Pages.

Gökalp işcan et al . . . , Antimicrobial Screen of Mentha piperita Essential Oils, Journal of Agricultural and Food Chemistry, Nov. 14, 2002, vol. 50, pp. 3943-3946, Anadolu University, Eskişehir, Turkey.

Glycerin, www.robholland.com/Nursing/Drug_Guide/data/monographframes/G019.html, Aug. 7, 2019.

Ashish Rawson, GC Method Validation for the Analysis of Menthol in Suppository Pharmaceutical Dosage Form, International Journal of Analytical Chemistry, vol. 2017 Article ID 1728414, Mar. 6, 2017, Saudi Arabia.

* cited by examiner

‡ imported from a related application

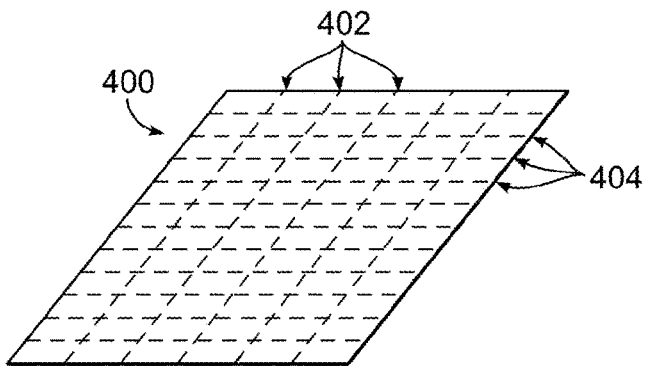
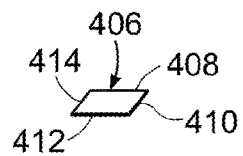
FIG. 4A-1　　　　　FIG. 4A-2
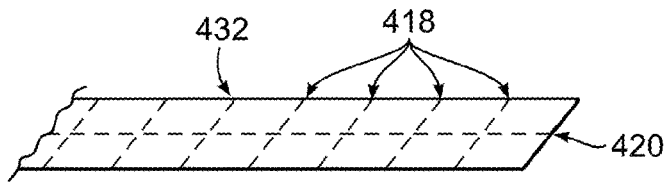
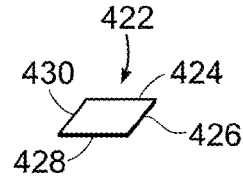
FIG. 4B-1　　　　　FIG. 4B-2
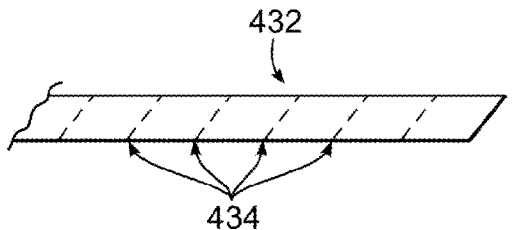
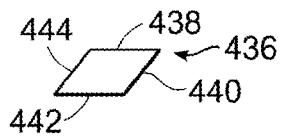
FIG. 4C-1　　　　　FIG. 4C-2
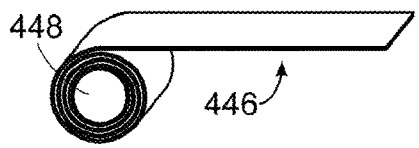
FIG. 4D-1　　　　　FIG. 4D-2
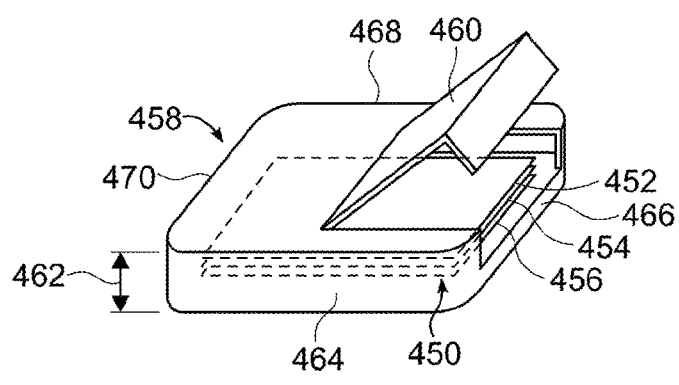
FIG. 4E

CANNABINOID, MENTHOL AND CAFFEINE DISSOLVABLE FILM COMPOSITIONS, DEVICES AND METHODS

CROSS-REFERENCE TO RELATED APPLICATIONS

This application claims priority to and the benefit of U.S. Provisional Patent Application Ser. No. 62/726,713 filed Sep. 4, 2018 and U.S. patent application Ser. No. 16/419,336 filed May 22, 2019, the disclosures of which is incorporated herein by reference in its entirety.

FIELD

The aspects of the present disclosure relate to compositions including active agents such as cannabinoids, caffeine and menthol.

BACKGROUND

There is a need for novel consumable compositions to quickly and easily ingest healthy, therapeutic and nutritionally beneficial ingredients, such pain relievers, vitamins and caffeine. Some current products include various nutritional and energy drinks may be useful to supply such ingredients, but can take too much time to ingest for people who are on the go and want a faster and more easily ingested solution.

It is an object of the present disclosure to provide an easily and quickly ingestible products that will provide nutritional, energy inducing and therapeutic ingredients to the consumer.

The accompanying drawings illustrate presently preferred embodiments of the present disclosure, and together with the general description given above and the detailed description given below, serve to explain the principles of the present disclosure.

BRIEF DESCRIPTION OF THE DRAWINGS

The accompanying drawings illustrate presently preferred embodiments of the present disclosure, and together with the general description given above and the detailed description given below, serve to explain the principles of the present disclosure.

FIG. 4A-1 is illustrative of a perspective view of an exemplary film sheet embodiment of the present disclosure;

FIG. 4A-2 is illustrative of a perspective view of an exemplary separated segment of the exemplary film sheet embodiment of FIG. 4A-1;

FIG. 4B-1 is illustrative of a perspective view of an exemplary film strip embodiment of the present disclosure;

FIG. 4B-2 is illustrative of a perspective view of an exemplary separated segment of the exemplary film strip embodiment of FIG. 4B-1;

FIG. 4C-1 is illustrative of a perspective view of another exemplary film strip or tape embodiment of the present disclosure;

FIG. 4C-2 is illustrative of a perspective view of an exemplary separated segment of the exemplary film s strip or tape embodiment of FIG. 4C-1;

FIG. 4D-1 is illustrative of a perspective view of another exemplary film sheet embodiment of the present disclosure;

FIG. 4D-2 is illustrative of a perspective view of an exemplary separated segment of the exemplary film strip or tape embodiment of FIG. 4D-1; and FIG. 4E illustrate an exemplary embodiment for packaging the segments of FIG. 4A-2, 4B-2 or 4C-2.

SUMMARY

Figure 1:
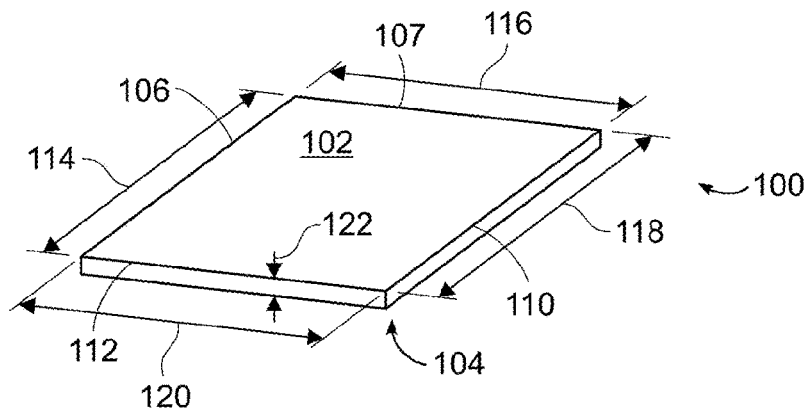
FIG. 1 is a perspective view of an embodiment of the present disclosure.

These and other aspects and advantages of the exemplary embodiments will become apparent from the detailed description. Additional aspects and advantages of the present disclosure will be set forth in the description that follows, and in part will be obvious from the description, or may be learned by practice of the present disclosure. Moreover, the aspects and advantages of the present disclosure may be realized and obtained by means of the instrumentalities and combinations particularly pointed out in the appended claims.

In one embodiment, a dissolvable thin oral tape, film or strip or segment thereof is provided. The dissolvable thin oral tape, film or strip or segment thereof includes a film former; at least one cannabinoid is in an amount of from about 0.1 wt % to about 10 wt %; menthol is in an amount of from about 0.1 wt % to about 20 wt %; caffeine in an amount of from about 0.1 wt % to about 30 wt %; and vitamins in an amount of from about 0.01 wt % to about 30 wt %.

In another embodiment, a dissolvable thin oral tape, film or strip or segment thereof is provided. The dissolvable thin oral tape, film or strip or segment thereof includes a film former including at least one of algin and pullulan; a plasticizer including glycerin; an emulsifier including polysorbate 80; full spectrum hemp oil in an amount of from about 0.1 wt % to about 10 wt %; menthol is in an amount of from about 0.1 wt % to about 20 wt %; caffeine in an amount of from about 0.1 wt % to about 30 wt %; and vitamins in an amount of from about 0.01 wt % to about 30 wt % and includes vitamins B2, B3, B5, B6 and B7.

In one embodiment, a method of treating pain of a mammal and stimulating the brain and central nervous system of the mammal using a therapeutic composition is provided. The therapeutic composition includes a dissolvable thin oral tape, film or strip or segment thereof. The dissolvable thin oral tape, film or strip or segment thereof includes a film former including at least one of algin and pullulan; a plasticizer including glycerin; an emulsifier including polysorbate 80; full spectrum hemp oil in an amount of from about 0.1 wt % to about 10 wt %; menthol is in an amount of from about 0.1 wt % to about 20 wt %; caffeine in an amount of from about 0.1 wt % to about 30 wt %; and vitamins in an amount of from about 0.01 wt % to about 30 wt % and includes vitamins B2, B3, B5, B6 and B7. The method includes orally administering the therapeutic composition to an oral cavity of the mammal.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by embodiments of the present disclosure. As used herein, "about" may be understood by persons of ordinary skill in the art and can vary to some extent depending upon the context in which it is used. If there are uses of the term which are not clear to persons of ordinary skill in the art, given the context in which it is used, "about" may mean up to plus or minus 10% of the particular term.

The terms "%", "% by weight", "weight %" and "wt %" are all intended to mean unless otherwise stated, percents by weight based upon a total weight of 100% end composition weight. Thus 10% by weight means that the component constitutes 10 wt. parts out of every 100 wt. parts of total composition.

The terms "oral acceptable" or "dentally acceptable" means the compound, substance or device may be administered to or into the oral cavity and/or surfaces of the oral cavity, including the teeth and gums, without substantial harmful effects to the oral cavity and/or its surfaces.

The term "pharmaceutically acceptable" means that which is useful in preparing a pharmaceutical composition that is generally non-toxic and is not biologically undesirable and includes that which is acceptable for veterinary use and/or human pharmaceutical use.

The aspects of the disclosed embodiments relate to a dissolvable oral thin tape, film or strip or segments thereof (e.g., a thin oral tape, film or strip or segments thereof) for the delivery of an active agent(s). The aspects of the disclosed embodiments also relate to processes for the preparation of, intermediates used in the preparation of the dissolvable oral thin tape, film or strip or segments thereof compositions or devices containing healthy, therapeutic and nutritionally beneficial ingredients and the uses of such compositions in the treatment of disorders or application of specified agents contained therein.

The aspects of the present disclosure relate to a dissolvable oral thin tape, film or strip or segments thereof compositions or devices used to relieve local and/or systemic pain (i.e., analgesics) and/or inflammation as well as healthful ingredients (such as, for example, vitamins) and a stimulant (such as, for example, caffeine), methods of making such compositions and methods of using such compositions including, for example, orally administered (e.g., placed in the mouth) compositions including pharmaceutical compositions, including analgesic and/or anti-inflammatory pharmaceutical compositions for the treatment of pain and/or inflammation, that contain a pharmaceutically effective amount of a pharmaceutically acceptable and effective cannabinoid, a pharmaceutically effective amount of menthol, a pharmaceutically and/or stimulant effective amount of stimulant and a pharmaceutically acceptable carrier, for example, a dissolvable thin oral tape, film or strip or segments thereof, the latter that can be obtained by, for example, cutting the dissolvable thin oral tape, film or strip and/or by manufacturing the dissolvable thin oral tape, film or strip with precut segments (e.g., with perforated edges) that can be separated using the perforated edges. Such dissolvable oral tape, film or strip or segments thereof compositions or devices may also include, for example, oral care compositions for the treatment of local and/or general overall pain as well as oral or dental pain, including oral care analgesic and/or anti-inflammatory compositions, for the treatment of local and/or general overall pain and/or oral or dental pain and/or inflammation that contain a pharmaceutically effective amount of an oral or dental acceptable and effective cannabinoid, a pharmaceutically effective amount of menthol, a pharmaceutically and/or stimulant effective amount of stimulant and an oral or dental acceptable carrier, for example, the a dissolvable thin oral tape, film or strip or segments thereof. Such a dissolvable thin oral tape, film or strip or segments thereof compositions or devices may also include, for example, analgesic and/or anti-inflammatory pharmaceutical compositions for the treatment of local and/or systemic pain and/or inflammation that contain a pharmaceutically effective amount of a pharmaceutically acceptable and effective cannabinoid, a pharmaceutically effective amount of menthol, a pharmaceutically and/or stimulant effective amount of stimulant and a pharmaceutically acceptable carrier, for example, a dissolvable thin oral tape, film or strip or segments thereof.

A dissolvable thin oral tape, film or strip or segments thereof refers to a product used to administer active ingredients (e.g., cannabinoids, menthol, caffeine, vitamins, etc.) via absorption in the mouth (mucosaly, buccally or sublingually), the stomach (gastrically), and/or via the small intestines (enterically). The dissolvable thin oral tape, film or strip or segments thereof are edible and pharmaceutically acceptable. A dissolvable thin oral tape, film or strip or segments thereof can be prepared typically using hydrophilic polymers that rapidly dissolves on the tongue or buccal cavity, delivering the active ingredients to the systemic circulation via dissolution when contact with liquid is made. The dissolvable thin oral tape, film or strip or segments thereof can also be used to adhere to mucosal tissue (e.g., at least one of mouth, nose, eye, vagina, and rectum), thereby locally and/or systemically delivering the active ingredient. As such, it is appreciated that those of skill in the art understand that reference to a thin film for use with mucosal tissue, such as nose, eye, vagina, and rectum, as an "oral thin film" or OTF is appropriate and acceptable. The dissolvable thin oral tape, film or strip or segments thereof can be placed, for example, on or around the tongue, the roof of the mouth, on the soft palate at back roof of the mouth, and even the epiglottis. The dissolvable thin oral tape, film or strip or segments thereof are sized and shaped to be place in the mouth and consumed orally.

The combination of cannabinoid and menthol as well as vitamins and a stimulant into a single therapeutic composition, for example, a dissolvable thin oral tape, film or strip or segments thereof, can provide improved and better focused delivery of the actives to a patient than applying the cannabinoid, menthol, vitamins and stimulant separately.

Orally administered including a dissolvable thin oral tape, film or strip or segments compositions or devices include products which, in the ordinary course of usage, can be placed in the mouth (e.g., on or under the tongue or as included above) to release the active ingredients (e.g., cannabinoid, menthol, vitamins, stimulant, etc.) therein, for example, from the dissolving of the dissolvable thin oral tape, film or strip or segments to release of the contents thereof and to deliver them in and through the mouth tissues and/or through the gastrointestinal tract after passage thereto from the mouth, after dissolution of the dissolvable thin oral tape, film or strip or segments thereof in the mouth or being swallowed before complete dissolution takes place for purposes of administration of the healthy, therapeutic and nutritionally beneficial ingredients contained therein. Oral cavity includes teeth, tissues (including mucous membranes and cheek tissue in the oral cavity) and the surfaces thereof present in mouth. The dissolvable thin oral tape, film or strip or segments thereof compositions may, for example, be administered to patients with oral pain, such as tooth pain, and pain from gums or cheeks following dental procedures, as wells as patients with bleeding gums or areas in the mouth that are suspect to infection as well as systemic pain in other parts of the body.

"Pain" as referred to herein for the composition and method embodiments of the current disclosure and for which an analgesic or pain relieving or pain treating composition or component thereof treats includes, but is not limited to local pain, systemic pain, oral pain, dental pain and general pain, regardless of the location on the body to which the embodiment of the current disclosure is administered.

"Anti-inflammatory" as referred to herein for the composition and method embodiments of the current disclosure and for which an anti-inflammatory composition or component thereof treats includes, but is not limited to local inflammation, systemic inflammation, oral inflammation, dental inflammation and general inflammation, regardless of the location on the body to which the embodiment of the current disclosure is administered.

Cannabinoids are an active agent and a class of chemical compounds that can be derived from plants (phytocannabinoids) or synthetically produced. Cannabinoids can have local and systemic analgesic, pain relieving, pain treating and anti-inflammatory therapeutic properties. Cannabinoids may also have other medical benefits and/or be useful in treating other medical conditions including, for example, reduction of anxiety and depression, reduction of symptoms like nausea, vomiting and pain related to cancer treatments, reduction of acne, protection of the neural system and benefits for the heart and circulatory system by the lowering of blood pressure. Cannabinoids can also have therapeutic value as a nutrient and can be included in composition and method embodiments of the present disclosure in an effective amount to perform that function.

Examples of phytocannabinoids include Cannabidiol (CBD) including, for example, CBD oil, Cannabinol (CBN) and tetrahydrocannabinol (THC), the latter being a known psychotropic compound and the first two being non-psychotropic. Cannabis and hemp plants can exhibit wide variation in the quantity and type of cannabinoids they produce. Selective breeding of the plants can be used to control the genetics of plants and modify the cannabinoids produced by the plant. For example, there are strains that are used as fiber (commonly called hemp) and, as a result, have been bred such that they are low in psychoactive chemicals like THC. Such strains (e.g., hemp) used in medicine are, for example, often bred for high CBD content and have minimal levels of THC (less than 0.3%). Examples of oral or pharmaceutically effective cannabinoids include CBD (for example, CBD oil). Cannabinoid, including, for example, phytocannabinoids including CBD, can be in an amount of about 0.1 wt % to about 10 wt %, about 0.1 wt % to about 5 wt %, about 1 wt % to about 3 wt %, about 2 wt %, about 3 wt %. Full spectrum CBD or hemp oil can be in an amount of about 0.1 wt % to about 10 wt %, about 0.1 wt % to about 5 wt %, about 1 wt % to about 3 wt %, about 2 wt %, about 3 wt %. Unit dosage formulations of the embodiments of the present disclosure can include cannabinoid, for example, a phytocannabinoid (including for example, CBD) in the amount of about 1 mg. to about 60 mg., about 2 mg. to about 45 mg., about 2 mg., about 30 mg., about 45 mg. Unit dosage formulations of the embodiments of the present disclosure can include CBD in the amount of about 1 mg. to about 60 mg., about 2 mg. to about 45 mg., about 2 mg., about 30 mg., about 45 mg. Unit doses of CBD oil and hemp oil (including full spectrum CBD oil and full spectrum hemp oil) content can include an amount of about 1 mg. to about 60 mg., about 2 mg. to about 45 mg., about 2 mg., about 30 mg., about 45 mg. An effective amount of cannabinoid includes an analgesic, pain relieving, pain treating or anti-inflammatory amount of cannabinoid.

Cannabinoids, for example, CBD can have a local and/or a systemic effect and may reduce pain imparting and regulating the endocannabinoid (neurotransmitter of the nervous system) receptor activity. The subsequent body functions that may be regulated include pain, sleep, appetite and immune system response (through, at least, in part, by reducing inflammation).

For the purpose of the present disclosure, the word "cannabinoid" refers to one or more cannabinoids or cannabinoid compounds or oils or extracts from plants (for example, hemp including hemp oil, CBD oil, full spectrum hemp oil and full spectrum CBD oil) that include one or a plurality of phytocannabinoids.

Full spectrum hemp oil is oil derived from the entire plant except the flower (which contains THC) and can have over 85 phytocannabinoids which can have a positive synergistic effect as compared to compositions having fewer cannabinoids. There may also be benefits to other components of it (e.g., terpenes). Such benefits and effect may include faster penetration and/or permeation of the therapeutic components thereof. Full spectrum hemp oil can include full spectrum hemp oil that has been purified to include less than the below stated amounts of one or more of the following impurities:

Aflatoxins B1, 82, G1, G2 (fats, oils, lecithin, egg powder): <0.1 µg/kg of each of Aflatoxin B1, Aflatoxin B2, Aflatoxin G1 and Aflatoxin G2, sum of all positive Aflatoxins <0.4 µg/kg.

GlyphosatelAMPAiGlufosinate: <0.1 mg/kg of each of Glufosinate, Glyphosate and Aminomethylphosphonic acid (AMPA)

Mercury: <0.02 mg/kg

Arsentic: <0.03 mg/kg

Cadmium: <0.01 mg/kg

Lead: <0.05 mg/kg

Menthol is an active agent and an organic compound that can be made synthetically or obtained from mint oils such as corn mint and peppermint. Medicinally, it been found that menthol can have anesthetic (e.g., local) by, for example, blocking nerve signal transmission) and counterirritant properties as well as anti-inflammatory properties (e.g., systemic and local) when administered to a patient. Furthermore, menthol is a vasodilator that can accelerate the transport of active in the circulatory system. In general, the action of local anesthetics can restrict to the site of application and rapidly reverses upon diffusion from the site of action in the nerve. Local anesthetics can also serve an important function in providing peripheral pain relief. Topical administration of pain-relieving anesthetics can provide important advantages over systemic or local, non-topical administration. Menthol can be in an amount of about 0.1 wt % to about 20 wt %, about 0.1 wt % to about 17 wt %, about 0.1 wt % to about 1 wt %, about 16 wt % to about 17 wt %, about 0.15 wt %, about 16 wt %, about 17 wt %. Unit dosage formulations of the embodiments of the present disclosure can include menthol in the amount of about 0.1 mg. to about 300 mg., about 190 mg., to about 191 mg., about 285 mg. An effective amount of menthol includes an anesthetic, pain reducing (e.g., analgesic) or anti-inflammatory effective amount of menthol.

Menthol may be stabilized using methods know in the art, such as, for example, mixing it with about 0.1 wt % to about 10 wt %, about 0.5 wt % to about 5 wt % of a surfactant including edible nonionic surfactants and ionic surfactants, such as, for example, sucrose fatty acid ester, polysorbate (e.g., polysorbate 80), hydrogenated castor oil (e.g., polyoxyethylene hydrogenated castor oil), cocamidopropyl betaine, etc.

Embodiments of the present disclosure can include an energy inducing ingredient that can increase attention and reaction speed. Such an energy inducing ingredient can include a stimulant, such as, for example, caffeine. "Stimulant" refers to any substance that can act to increase activity of the central nervous system and that excites any bodily function, and in particular substances that stimulate, e.g., the brain and central nervous system. A substance is considered to be a stimulant if it is capable of inducing and/or increasing alertness, elevated mood, wakefulness, increased speech, elevated motor activity, and/or decreased appetite. When it reaches your brain, the most noticeable effect is alertness. One who ingests caffeine can feel more awake and alert as well as less tired. It can also have other therapeutic benefits and can be a common ingredient in medications to treat or manage drowsiness, headaches, and migraines. A "stimulant effective amount" and a "pharmaceutically effective amount of a stimulant" are both considered to be dose levels of a stimulant capable of achieving such effects. In the present embodiments, caffeine can be in an amount of about 0.1 wt % to about 30 wt %, about 9 wt % to about 27 wt %, about 9 wt % to about 10 wt %, about 26 wt % to about 27 wt %, about 9 wt %, about 26 wt %. Unit dosage formulations of the embodiments of the present disclosure can include caffeine in the amount of about 1 mg to about 500 mg, about 10 mg to about 450 mg, about 10 mg, about 300 mg, about 450 mg.

Embodiments of the present disclosure may also optionally include an effective amount of THC. Unit dosage formulations of the embodiments of the present disclosure can include THC in the amount of about 0.1 mg. to about 10 mg., about 1 mg. to about 10 mg., about 4 mg. to about 6 mg. about 5 mg. In addition to the other benefits that can be provided by other cannabinoids, THC may also relieve stress and be a sleeping aid.

The aspects of the present disclosure also relate to dissolvable thin oral tape, film or strip or segments thereof compositions or devices for the delivery of, for example, pharmaceutical compositions, including analgesic pharmaceutical compositions, that contain a pharmaceutically effective amount of a pharmaceutically acceptable and effective cannabinoid, a pharmaceutically effective amount of menthol and a pharmaceutically and/or stimulant effective amount of a stimulant (e.g., caffeine) and dissolvable thin oral tape, film or strip or segments thereof composition or device, including oral care analgesic dissolvable thin oral tape, film or strip or segments thereof, that contain a pharmaceutically effective amount of an oral or dental acceptable and effective cannabinoid and a pharmaceutically effective amount of menthol and a pharmaceutically and/or stimulant effective amount of a stimulant (e.g., caffeine).

An embodiment of the present disclosure relates to dissolvable thin oral tape, film or strip or segments thereof composition or device including a pharmaceutically effective amount of a pharmaceutically acceptable and effective cannabinoid, for example, a phytocannabinoid and full spectrum CBD or hemp oil, and a pharmaceutically effective amount of a pharmaceutically acceptable and effective anesthetic menthol, a pharmaceutically and/or stimulant effective amount of a stimulant (e.g., caffeine) along with a pharmaceutically acceptable carrier.

An embodiment of the present disclosure relates to a dissolvable thin oral tape, film or strip or segments thereof composition or device including a pharmaceutically effective amount of a pharmaceutically acceptable and effective cannabinoid, for example, a phytocannabinoid and full spectrum CBD or hemp oil, and a pharmaceutically effective amount of a pharmaceutically acceptable and effective anesthetic menthol, a pharmaceutically and/or stimulant effective amount of a stimulant (e.g., caffeine) along with a pharmaceutically acceptable carrier.

Another embodiment of the present disclosure relates to a dissolvable thin oral tape, film or strip or segments thereof composition or device including a pharmaceutically effective amount of an oral or dental acceptable and effective cannabinoid, for example, a phytocannabinoid and full spectrum CBD or hemp oil, and a pharmaceutically effective amount of menthol and a pharmaceutically and/or stimulant effective amount of a stimulant (e.g., caffeine) along with a pharmaceutically acceptable carrier.

Another embodiment of the present disclosure relates to a dissolvable thin oral tape, film or strip or segments thereof composition or device including a pain reducing (e.g., analgesic and/or anesthetic) and/or anti-inflammatory pharmaceutically effective amount of a pharmaceutically acceptable and effective cannabinoid, for example, a phytocannabinoid and full spectrum CBD or hemp oil, and a pain reducing (e.g., analgesic and/or anesthetic) and/or anti-inflammatory pharmaceutically effective amount of a pharmaceutically acceptable and effective menthol and a pharmaceutically and/or stimulant effective amount of a stimulant (e.g., caffeine) along with a pharmaceutically acceptable carrier.

Another embodiment of the present disclosure relates to a dissolvable thin oral tape, film or strip or segments thereof composition or device including a pain reducing (e.g., analgesic and/or anesthetic) and/or anti-inflammatory pharmaceutically effective amount of an oral or dental acceptable and effective cannabinoid, for example, a phytocannabinoid and full spectrum CBD or hemp oil, and a pain reducing (e.g., analgesic and/or anesthetic) and/or anti-inflammatory pharmaceutically effective amount of an oral or dental acceptable and effective menthol and a pharmaceutically and/or stimulant effective amount of a stimulant (e.g., caffeine) along with a pharmaceutically acceptable carrier.

Another embodiment of the present disclosure relates to a dissolvable thin oral tape, film or strip or segments thereof composition or device including an oral or dental pain reducing (e.g., analgesic and/or anesthetic) and/or anti-inflammatory pharmaceutically effective amount of an oral or dental acceptable and effective cannabinoid, for example, a phytocannabinoid and full spectrum CBD or hemp oil, and an oral or dental pain reducing (e.g., analgesic and/or anesthetic) and/or anti-inflammatory pharmaceutically effective amount of an oral or dental acceptable and effective menthol and a pharmaceutically and/or stimulant effective amount of a stimulant (e.g., caffeine) along with a pharmaceutically acceptable carrier.

Another embodiment of the present disclosure relates to a dissolvable thin oral tape, film or strip or segments thereof composition or device including a pain reducing (e.g., analgesic and/or anesthetic) and/or anti-inflammatory pharmaceutically effective amount of a pharmaceutically acceptable and effective cannabinoid, for example, a phytocannabinoid, and a pain reducing (e.g., analgesic and/or anesthetic) and/or anti-inflammatory pharmaceutically effective amount of a pharmaceutically acceptable and effective menthol and a pharmaceutically effective amount of a stimulant (e.g., caffeine) along with a pharmaceutically acceptable carrier.

Another embodiment of the present disclosure relates to a dissolvable thin oral tape, film or strip or segments thereof composition or device including cannabinoid, for example, CBD and full spectrum CBD or hemp oil, in an amount of about 0.1 wt % to about 10 wt %, about 0.1 wt % to about 5 wt %, about 1 wt % to about 3 wt %, about 2 wt %, about 3 wt % and menthol in an amount of about 0.1 wt % to about 20 wt %, about 0.1 wt % to about 17 wt %, about 0.1 wt % to about 1 wt %, about 16 wt % to about 17 wt %, about 0.15 wt %, about 16 wt %, about 17 wt % and a stimulant (e.g., caffeine) in an amount of about 26 wt % to about 27 wt %, about 9 wt %, about 26 wt % along with a pharmaceutically acceptable carrier.

In another embodiment of the present disclosure, the a dissolvable thin oral tape, film or strip or segments thereof composition or device including cannabinoid, for example, phytocannabinoids and full spectrum CBD or hemp oil, in an amount of about 0.1 wt % to about 10 wt %, about 0.1 wt % to about 5 wt %, about 1 wt % to about 3 wt %, about 2 wt %, about 3 wt %; and menthol in an amount of about 0.1 wt % to about 20 wt %, about 0.1 wt % to about 17 wt %, about 0.1 wt % to about 1 wt %, about 16 wt % to about 17 wt %, about 0.15 wt %, about 16 wt %, about 17 wt % and a stimulant (e.g., caffeine) in an amount of about 26 wt % to about 27 wt %, about 9 wt %, about 26 wt % along with a pharmaceutically acceptable carrier.

Hemp oil (also known as full spectrum hemp oil) can contain about 25% CBD, hemp oil breakdown w/w %: phytocannabinoids=about 5.70%, CBD=about 1.9% Total about 7.60%. Unit dose weight is about 0.55 grams/dose and will deliver about 10 mg. CBD, about 30 mg. phytocannabinoids and about 0.08 mg. THC (negligible). Phytocannabinoids comprise the following: as of 2016, there are 11 subclasses: (1) cannabigerol (CBG); (4) cannabichromene (CBC); (5) cannabinol (CBD); (7) cannabicyclol (CBL); (8) cannabinodiol (CBND); (9) cannabielsoin (CBE); (10) cannabitriol (CBT); and (11) miscellaneous types.

All of the embodiments included here are with the proviso that the sum of ingredients in the exemplary compositions does not exceed 100%.

The terms "treating" and "effective amount", as used herein, unless otherwise indicated, means reversing, alleviating, inhibiting the progress of, or preventing the disorder or condition to which such term applies, or one or more symptoms of such disorder or condition or achieving a desired physical effect. The term "treatment", as used herein, unless otherwise indicated, refers to the act of treating as "treating" is defined immediately above. The term "treating" also includes adjuvant and neo-adjuvant treatment of a subject.

Optional ingredients can include vitamins, such as, for example, vitamins as an additional nutritional supplement, such as B vitamins including, for example, vitamins, B2, B3, B5, B6, B12 and B7. These B vitamins can converts food into ATP (andensoine triphosphate) a form of useable body energy The amount of B vitamins can depend on which B vitamin is being added, but generally can range in an amount of from about 0.01 wt % to about 30 wt %, about 4 at % to about 6 wt %, about 25 wt % to about 27 wt %, about 16 wt % to about 18 wt %, about 5 wt %, about 26 wt %, about 17 wt %. The unit dose of B vitamins can depend on which B vitamin is being added, but generally can range in an amount from about 2 mg to about 300 mg.

Vitamin B2 is one of the optional vitamins that can be included in the embodiments of the present disclosure and can be incorporated, for example, as riboflavin 5'-phosphate. The amount of B2 in embodiments of the present disclosure can range in an amount of from about 1 wt % to about 30 wt %, about 4 wt % to about 6 wt %, about 25 wt % to about 27 wt %, about 16 wt % to about 18 wt %, about 5 wt %, about 26 wt %, about 17 wt %. The unit dose of B2 in embodiments of the present disclosure can range in an amount from about 5 mg to about 300 mg, about 5 mg, about 300 mg.

Vitamin B3 is one of the optional vitamins that can be included in the embodiments of the present disclosure and can be incorporated, for example, as niacinide. The amount of B3 in embodiments of the present disclosure can range in an amount of from about 5 wt % to about 50 wt %, about 4 wt % to about 6 wt %, about 7 wt % to about 9 wt %, about 45 wt % to about 47 wt %, about 6 wt %, about 9 wt %, about 47 wt %. The unit dose of B3 in embodiments of the present disclosure can range in an amount from about 2 mg to about 100 mg, about 50 mg, about 300 mg.

Vitamin B5 is one of the optional vitamins that can be included in the embodiments of the present disclosure and can be incorporated, for example, as calcium-pantothenate. The amount of B3 in embodiments of the present disclosure can range in an amount of from about 1 wt % to about 5 wt %, about 1 wt % to about 3 wt %, about 3 wt % to about 5 wt %, about 5 wt %, about 2 wt %, about 1 wt %. The unit dose of B5 in embodiments of the present disclosure can range in an amount from about 2 mg to about 100 mg, about 50 mg, about 300 mg.

Vitamin B6 is one of the optional vitamins that can be included in the embodiments of the present disclosure and can be incorporated, for example, as pryidoxyl 5' phosphate. The amount of B6 in embodiments of the present disclosure can range in an amount of from about 1 wt % to about 5 wt %, about 2 at % to about 3 wt %, about 4 wt % to about 5 wt %, about 2 wt %, about 3 wt %, about 4 wt %. The unit dose of B6 in embodiments of the present disclosure can range in an amount from about 2 mg to about 50 mg, about 2 mg, about 3 mg, about 50 mg.

Vitamin B7 is one of the optional vitamins that can be included in the embodiments of the present disclosure and can be incorporated, for example, as biotin D. The amount of B7 in embodiments of the present disclosure can range in an amount of from about 0.01 wt % to about 1 wt %, about 0.03 wt %, about 1 wt %, about 0.6 wt %. The unit dose of B2 in embodiments of the present disclosure can range in an amount from about 10 mg to about 30 mg, about 10 mg, about 30 mg.

An appropriate edible film carrier for use with embodiments of the present disclosure can be selected by one of ordinary skill in the art depending upon factors including the desired rate of dissolution, desired oral feel for the user, the compatibility of the thin film carrier and the active ingredients, production constraints, costs, or other factors. The film can also be thick or thin depending upon these same factors.

The desired rate for dissolution can vary depending of the specific application for the edible film. For example, for immediate delivery of the active ingredient, the film can be manufactured to rapidly dissolve in the oral cavity thus delivering the entire dosage of active ingredient at one time. The film can also be manufactured to dissolve over an extended period regulating the amount of active material delivered to the oral cavity over a desired length of time The other components that make of the matrix or carrier material of the dissolvable thin oral tape, film or strip or segments thereof composition or device of the present disclosure in which the above composition ingredients are includes are film formers, plasticizer, emulsifiers, coloring agents.

The primary ingredient for an edible film according to the present disclosure is the film former, which in most cases can be any water soluble film former. Film formers include but are not limited to pullulan, guar gum, pectin, xanthan gum, alginates (e.g., Alginic acid, also called algin), gelatin, starches (including corn, potato, rice or tapioca), modified starches, matltodextrins, wheat gluten, carboxymethylcellulose, carrageenan konjac, locust bean gum or combinations thereof. In some embodiments, some of these ingredients may have functions in addition to acting as a film former, for example, pullulan can be used to form a transparent film, algin can form a viscose gum binder, and corn starch can supply additional structure to the film. The amount of film former in embodiments of the present disclosure can generally range in an amount of from about 10 wt % to about 25 wt %.

The dissolvable thin oral tape, film or strip or segments thereof can be various lengths, but when administered to the mouth should be of a size that can conveniently fit therein and be of a size such that it is fast dissolving. The weight per strip may vary. The weight of the dissolvable thin oral tape, film or strip or segments thereof administered to the mouth may be in the ranges of about 50 mg to about 2000 mg, about 50 mg to about 110 mg, about 100 mg to about 110 mg, about 1000 mg to about 2000 mg, about 1100 mg to about 1200 mg, about 1700 mg to about 1800 mg, about 107 mg, about 1132 mg, about 1716 mg. The maximum dosing per embodiment of the present disclosure may also vary depending on the choice of active ingredient. Active ingredients can be delivered in a solid or liquid format and depending on dose levels, the Active ingredients can be oil or water soluble. Preferably, the dosage per serving is 1-2 embodiments of the present disclosure but may vary depending on the size of the individual strip and other factors known one skilled in the art.

Emulsifying agents include solubilizers and wetting agents and are exemplified by polyvinyl alcohol, sorbitan esters, cyclodextrins, benzyl benzoate, glyceryl monostearate, polyoxyethylene alkyl ethers, polyoxyethylene stearates, poloxamer, polyoxyethylene castor oil derivatives, hydrogenated vegetable oils, bile salts, polysorbates (e.g., polysorbate 80) and ethanol. The amount of emulsifier in embodiments of the present disclosure can generally range in an amount of from about 1 wt % to about 5 wt %. The emulsifier (e.g., polysorbate 80) can also stabilize the menthol.

Plasticizers may include glycerin, sorbitol, propylene glycol, polyethylene glycol, triacetin, triethyl citrate (TEC), acetyl triethyl citrate (ATEC) and other citrate esters. In some embodiments, some of these ingredients may have functions in addition to acting as a plasticizer, for example, glycerin can be used to stabilize oil in water and propylene glycol can be shelf life additive. The amount of plasticizer in embodiments of the present disclosure can generally range in an amount of from about 5 wt % to about 15 wt %.

Coloring agents may include FD & C coloring agents, natural coloring agents, and natural juice concentrates, pigments such as tartrazine, titanium oxide, silicon dioxide and zinc oxide.

Any standard manufacturing procedure known in the art may be used to manufacture the tape, film or strip or segments thereof of the present disclosure. For example, in a vessel (with or without mixing), one would add in order, water (about 50 wt % to about 70 wt %), plasticizer (e.g., glycerin), the active therapeutic or nutritional agents except menthol (e.g., CBD or full spectrum hemp oil, caffeine & vitamins), the remaining ingredients except for the menthol, emulsifying agent and the film former or formers (e.g., sweeteners, flavors, coloring agents, etc.), and the film former or if there is more than one, each separately (e.g., pullulan and algin). Next the menthol and emulsifying agent (e.g., polysorbate 80) are added together and mixed separately from the vessel to stabilize the menthol. The menthol and emulsifying agent mixture are then added to the vessel. The contents of the vessel can be optionally degassed. The contents of the vessel are then cast or spread into film and passed through a heat tunnel to flash off most of the water leaving about 5 wt % to about 15 wt % in the film. Leaving about 5 wt % to about 8 wt % can lead to the tape, film or strip or segments thereof not sticking to each other when they are placed in contact. Another way to minimize such sticking together is to leave a textured surface on the tape, film or strip or segments thereof such as surface areas 102 and 104 in FIG. 1, surface areas 202 and 204 in FIG. 2B and surface areas 208 and 210 in FIG. 2B. Such a texture can be created by not degassing the mixture before casting it into a film A suitable size of embodiments of the present disclosure include, for example, dissolvable thin oral tape, film or strip or segments thereof as illustrated in FIG. 1 which can include the shape of a square or rectangle 100 or other polygon shape (including, e.g., triangle, pentagon, hexagon, etc.) with surface areas 102 and 104 (on opposing sides) and the dimensions of sides 106, 107, 110 and 112, each ranging in length 114, 116, 118 and 120, respectively from about 0.5 cm. to about 5 cm. (including about 1 cm by about 1.5 cm, about 1 cm by about 3.3 cm, about 1.25 cm by about 4 cm) and thickness 122 ranging from about 0.5 mm to about 5.0 mm, about 0.5 mm to about 1.0 mm, about 1.0 mm to about 2.0 mm, about 2.0 mm to about 3.0 mm, about 3.0 mm to about 4.0 mm, about 4.0 mm to about 5.0 mm. In the embodiment of illustrated in FIG. 1 each of the surface areas 102 and 104 (on opposing sides) can range from about 0.25 $cm^2$ to about 25 $cm^2$, about 1.5 $cm^2$, about 3.3 $cm^2$, about 5 $cm^2$.

Figure 2A:
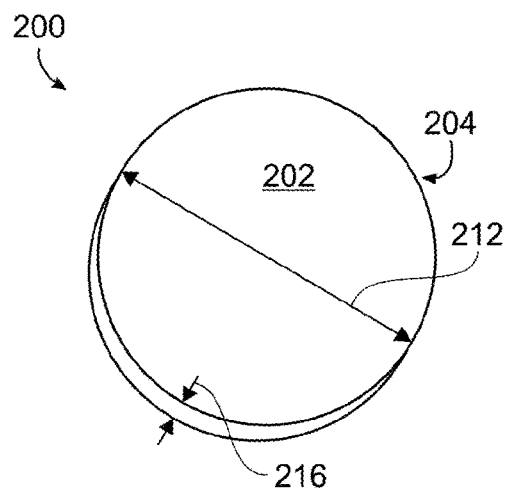
FIGS. 2A and 2B are perspective views of other embodiments of the present disclosure.
Figure 2B:
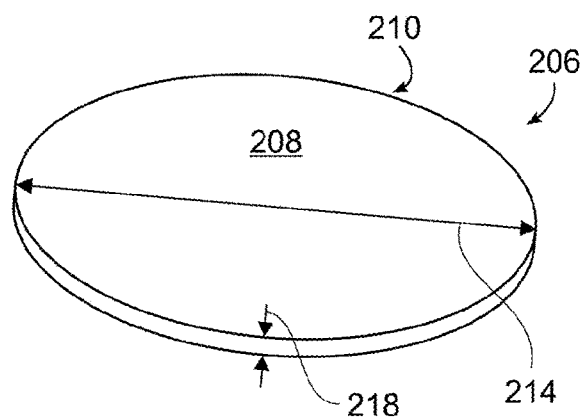

Other embodiment shapes can also include a circle 200 illustrated in FIG. 2A having a generally circular shape with surface areas 202 and 204 on opposing sides thereof or an ellipse 206 illustrated in FIG. 2B and with surface areas 208 and 210 on opposing sides thereof. Diameter 212 for FIG. 2A and diameter 214 for FIG. 2B can range from about 0.5 cm. to about 5 cm. The thickness 216 in circle 200 in FIG. 2A and thickness 218 ellipse 206 in FIG. 2B can range from about 0.5 mm to about 5.0 mm, about 0.5 mm to about 1.0 mm, about 1.0 mm to about 2.0 mm, about 2.0 mm to about 3.0 mm, about 3.0 mm to about 4.0 mm, about 4.0 mm to about 5.0 mm. Generally circular shape with each surface areas 202 and 204 on opposing sides thereof or an ellipse 206 illustrated in FIG. 2B and with surface areas each 208 and 210 on opposing sides thereof, each such surface can range from about 0.79 cm$^2$ to about 78 cm$^2$, about 1.5 cm$^2$, about 3.3 cm$^2$, about 5 cm$^2$.

Figure 3A:
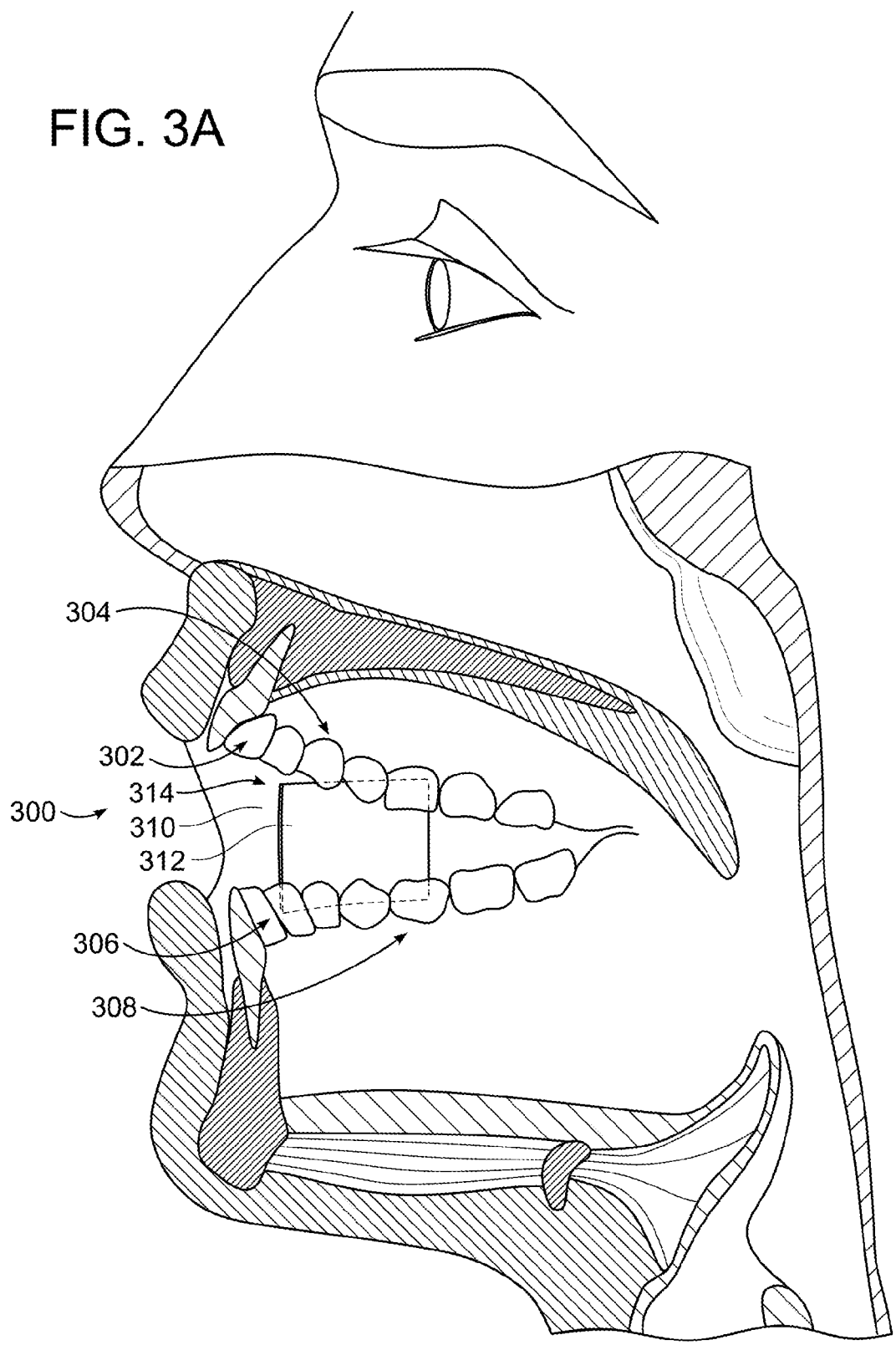
FIGS. 3A-3E illustrate an exemplary implementation of the aspects of the disclosed embodiments.
Figure 3B:
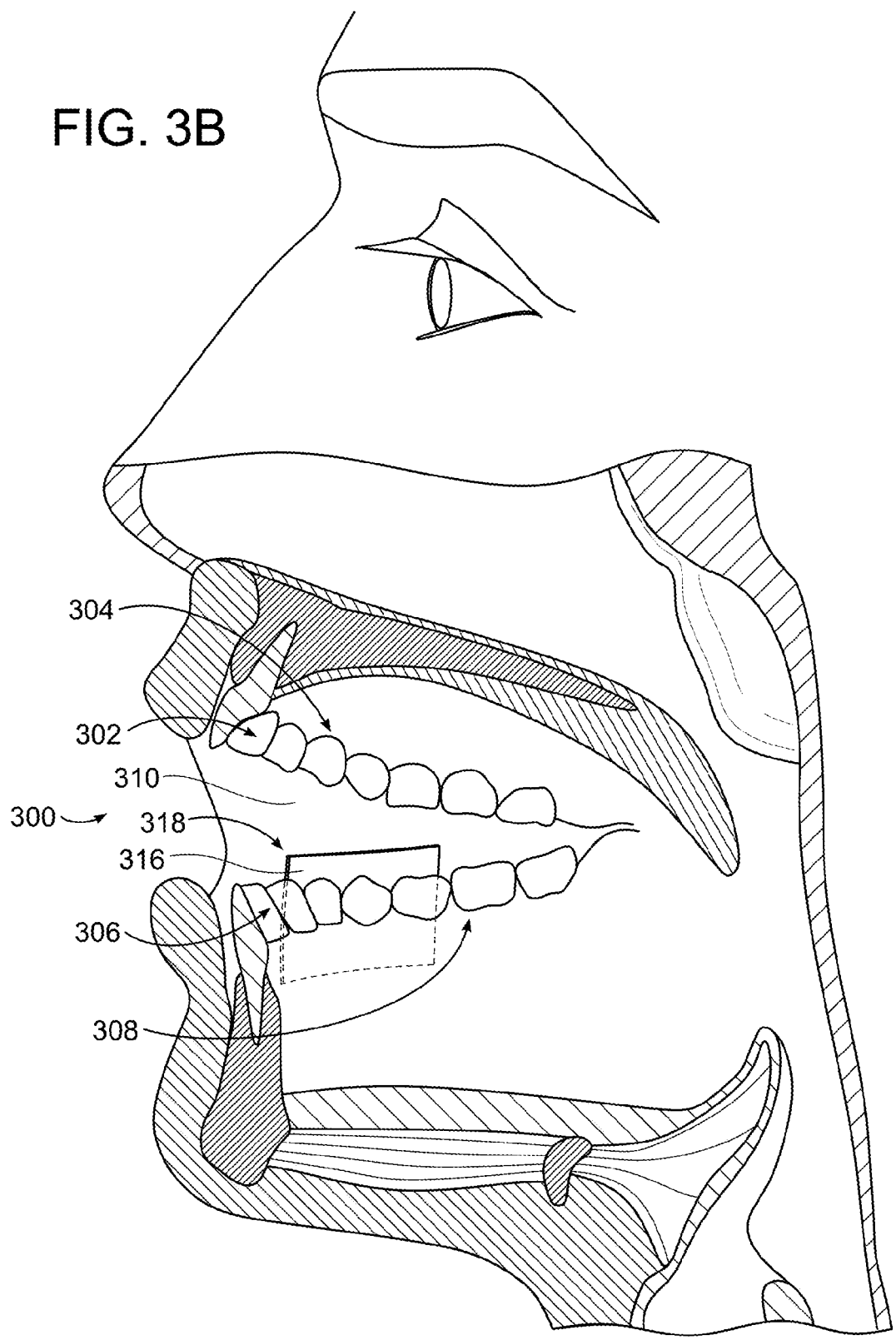

Embodiments showing possible placement are illustrated in FIGS. 3A-3E. FIGS. 3A and 3B show a cross-section of an oral cavity 300 including an upper row of teeth 302, upper gum 304, lower row of teeth 306, lower gum 308 and cheek surface 310 inside the oral cavity. One of the embodiments of the present disclosure 312 (that includes one of the formulation embodiments of the present disclosure) can be positioned against the cheek surface 310 at 314. An alternative is an embodiment of the present disclosure 316 positioned against cheek surface 310 at 318 so that the embodiment 316 is also adjacent lower gum 308.

Figure 3C:
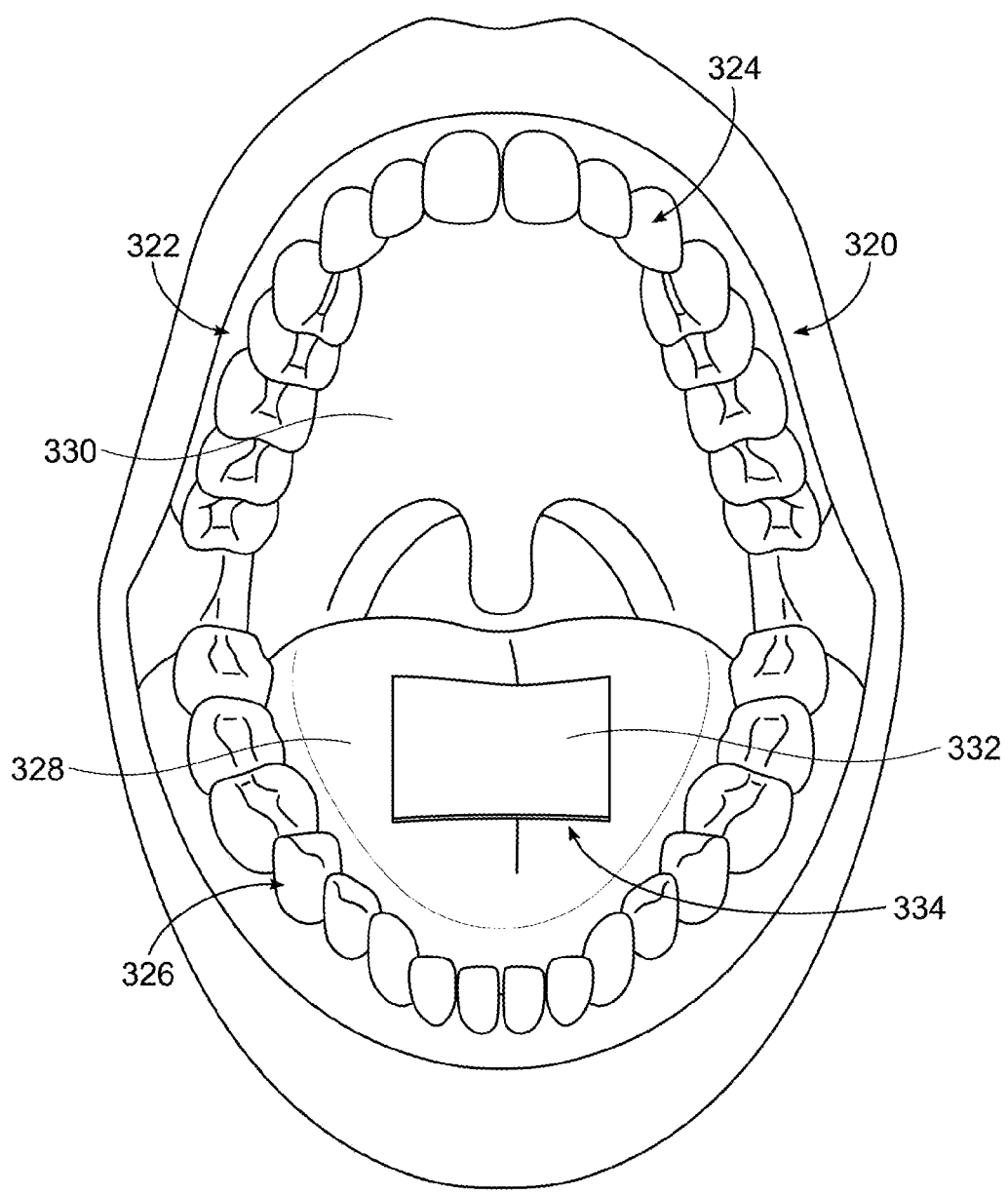
Figure 3D:
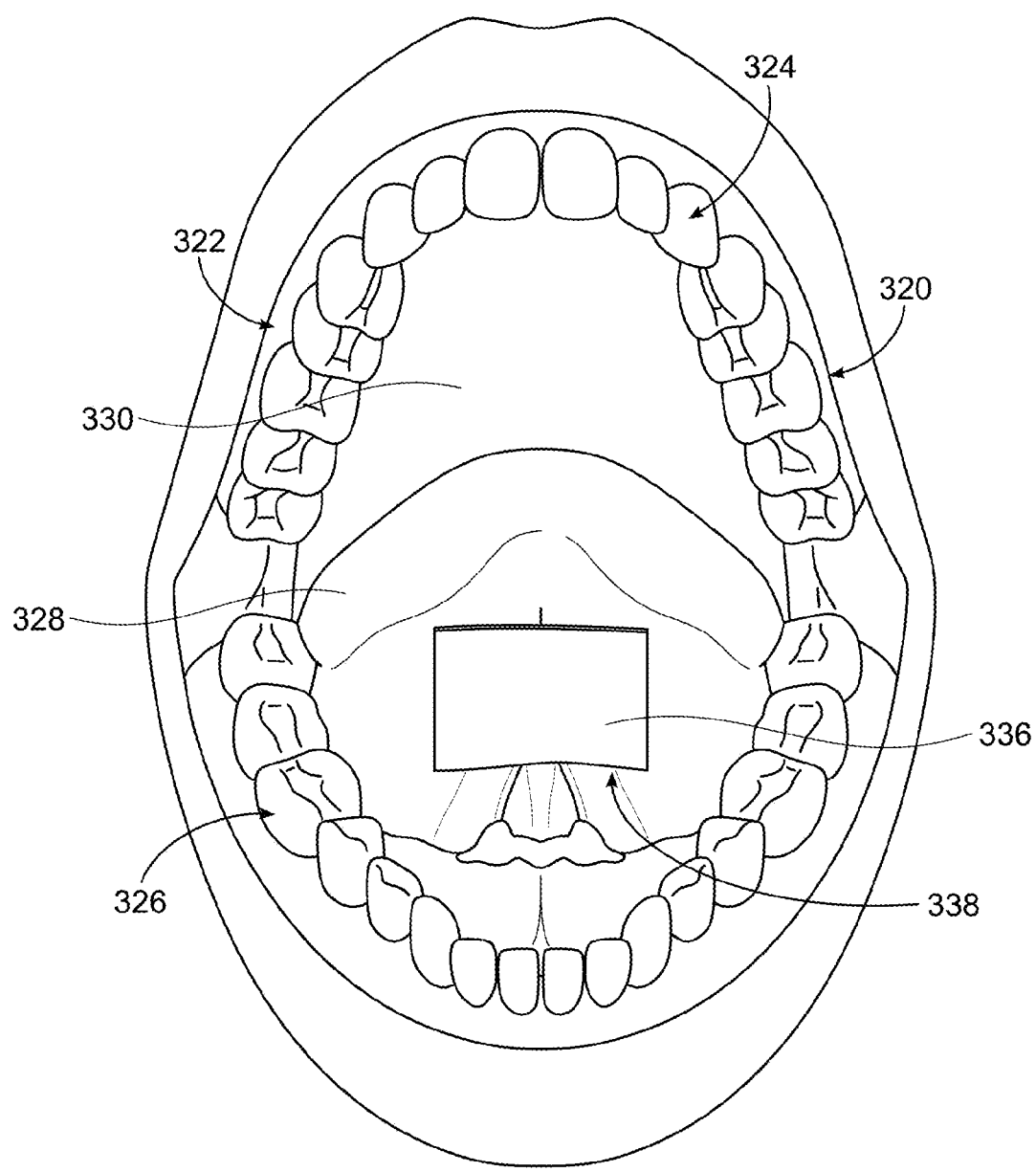
Figure 3E:
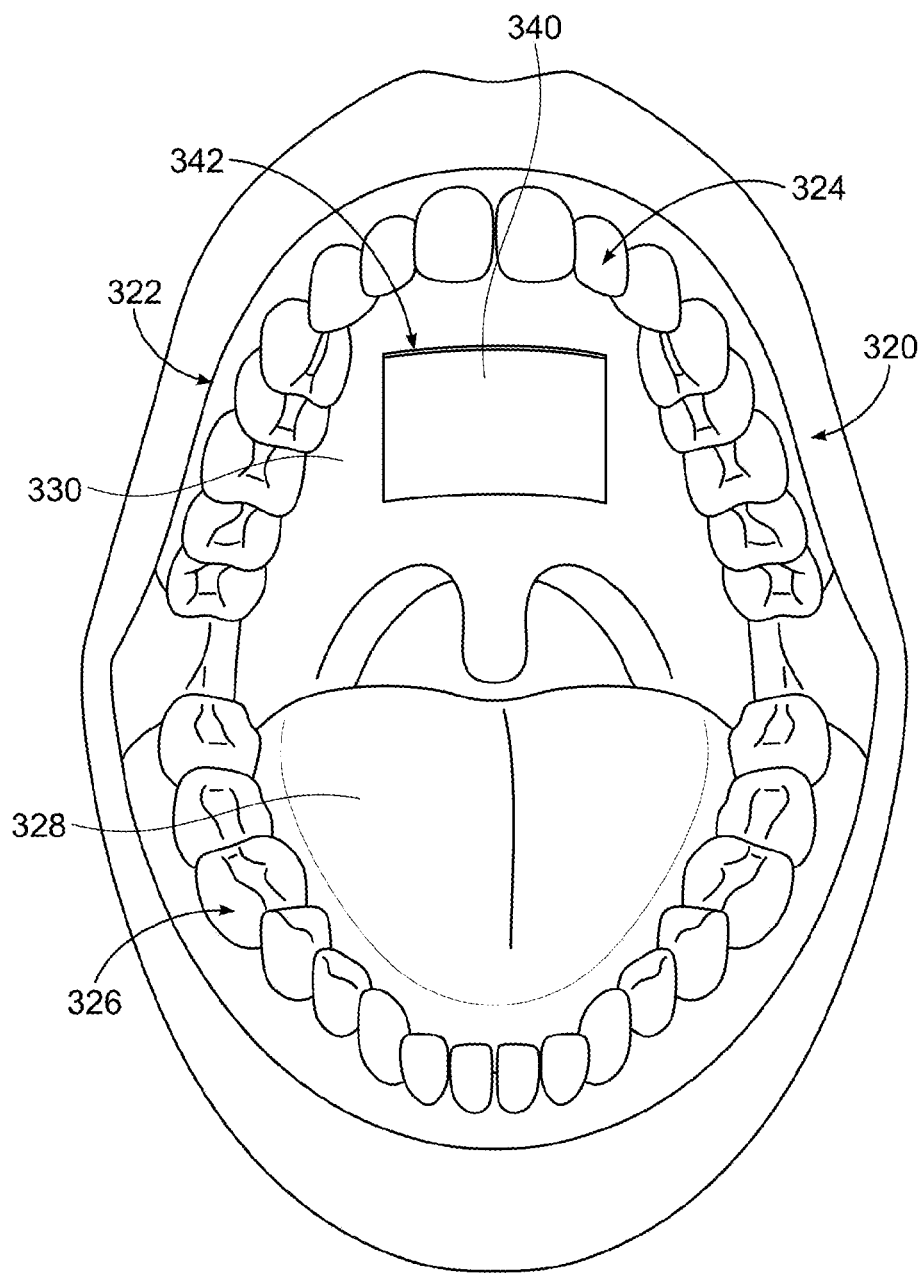

FIGS. 3C, 3D and 3E show an oral cavity 320 when viewed through an open mouth 322 and includes an upper row of teeth 324, lower row of teeth 326, tongue 328 and palate 330 inside the oral cavity. One of the embodiments of the present disclosure 332 (that includes one of the formulation embodiments of the present disclosure) can be positioned against the surface of the tongue 328 at 334. An alternative is an embodiment of the present disclosure 336 positioned can be positioned under the tongue 328 at 338. Another alternative is an embodiment of the present disclosure 340 can be positioned against the surface of the palate 330 at 342.

Although all surfaces of the embodiments of the present disclosure can be applied to the cheek or other oral surfaces to administer the agents included therein (e.g., CBD, menthol, caffeine, vitamins, etc.) for transdermal delivery into and through the tissues of the cheek surface as well as through the GI tract to bring about the intended local and/or systemic effect, the largest surfaces (e.g., surface areas 102 and 104 in FIG. 1, in FIG. 2A with surface areas 202 and 204 and in FIG. 2B and with surface areas 208 and 210) should preferably be placed against those oral surfaces.

The film can then be cut or divided into various forms and sizes of the embodiments of the present disclosure, e.g., dissolvable thin tape, film, section or strip or segments thereof including tape film or strip sections with perforations to separate them into segments thereof. Examples of such are shown in FIGS. 4A-4E. In FIGS. 4A-1 and 2, film sheet 400 includes vertical cut lines 402 and horizontal cut lines 404 in which once film sheet 400 is cut results in a plurality of segments of the embodiments of the present disclosure 406. The edges 408, 410, 412 and 414 of each segment 406 can be smooth if the cuts are made mechanically (e.g., scissors or a knife including a hot knife) or jagged if the cut lines are perforated, each edge depending on whether it is external or internal side to film sheet 400.

In FIGS. 4B-1 and 2, film strip 416 includes vertical cut lines 418 and horizontal cut line 420 in which once film strip 416 is cut results in a plurality of segments of the embodiments of the present disclosure 422. The edges 424, 426, 428 and 430 of each segment 422 can be smooth if the cuts are made mechanically (e.g., scissors or a knife including a hot knife) or jagged if the cut lines are perforated, each edge depending on whether it is external or internal side to film strip 416

In FIGS. 4C-1 and 2, film strip or tape 432 includes vertical cut lines 434 in which once film strip or tape 432 is cut results in a plurality of segments of the embodiments of the present disclosure 436. The edges 438, 440, 442 and 444 of each segment 436 can be smooth if the cuts are made mechanically (e.g., scissors or a knife including a hot knife) or jagged if the cut lines are perforated, each edge depending on whether it is external or internal to film strip or tape 432.

In FIGS. 4D-1 and 2, film strip or tape shown in FIG. 4B-1 or 4C-1 here as film strip or tape 446 can be packaged on a spool 448 prior to being separated into segments of the embodiments of the present disclosure 449 as shown in FIGS. 4B-2 and 4C-2.

In FIG. 4E, segments of the embodiments of the present disclosure shown in FIGS. 4A-4C here as a plurality of segments 450 that can be stacked or positioned adjacent one another is a container 458 with a lid 460 (e.g., a hinged lid), exemplified with segments 452, 454 and 456, although the number of stacked or positioned adjacent segments is not limited. The height 462 of container 458 can be sized to fit a plurality of segments stacked therein including, for example, 1-10 segments, 1-25 segments, 1-50 segments, etc. The sides 464, 466, 468 and 470 are of suitable dimension to be slightly larger (e.g., about 0.01 to about 0.25 cm, about 0.1 cm larger than a side of the segment placed therein) than the dimensions of the segments therein so that the latter fit therein.

In a further embodiment, a kit is disclosed. One example of such a kit is a kit including a composition or unit dose composition of one of the embodiments of the present disclosure including multiple unit doses and instructions for use.

These and other aspects and advantages of the exemplary embodiments will become apparent from the detailed description. Additional aspects and advantages of the present disclosure will be set forth in the description that follows, and in part will be obvious from the description, or may be learned by practice of the present disclosure. Moreover, the aspects and advantages of the present disclosure may be realized and obtained by means of the instrumentalities and combinations particularly pointed out in the appended claims.

Other optional ingredients include colorants, flavorings and flavor enhancers, preservatives, salivary stimulating agents, sweetening agents, fillers, stabilizers and buffers.

Sweetening agents, including pharmaceutically acceptable sweetening agents and sugar-free sweetening agents, can include, for example, saccharin, dextrose, sucrose, lactose, maltose, levulose, aspartame, Stevia (e.g., Stevia rebaudiana leaf/stem extract), sodium cyclamate, D-tryptophan, dihydrochalcones, acesulfame, monk fruit sweeteners and mixtures thereof. Sweetening agents can be generally used at levels of from about 0.005 wt % to about 5 wt %, by weight of the composition, preferably from about 2 wt % to about 3 wt %.

Fillers, including pharmaceutically acceptable fillers, can include, for example, fumed silica, calcium carbonate, talc, corns starch, clays, methacrylate powder, polyethylene/polypropylene beads, etc., including water soluble inert fillers, e.g., mannitol, xylitol, sucrose, lactose, maltodextrin, dextran, dextrin, modified starches, dextrose, sorbitol, and dextrates. Fillers can be generally used at levels of from about 15 wt % to about 40 wt %, by weight of the composition, preferably from about 20 wt % to about 30 wt %.

Certain embodiments of the present disclosure may contain at least one flavoring and/or odorant composition that renders the composition or film palatable. Flavoring agents can include, for example, wintergreen, peppermint, sweet mint, spearmint, vanillin, cherry, chocolate, cinnamon, clove, lemon, orange, raspberry, rose, spice, violet, herbal, fruit, strawberry, grape, pineapple, peach, kiwi, papaya, mango, coconut, apple, coffee, plum, watermelon, nuts, durean, green tea, grapefruit, banana, etc. Any effective flavor or odor may be used. The flavoring can be present in any effective amount, including, for example, in an amount ranging from about 0.5 to 40 wt. %, 1 to 30 wt. %, 5 to 15 wt. %, 0.5 to 15 wt. %. The flavorings may be natural or artificial, or combinations thereof.

Preservatives which here include anti-microbial agents and non-organic compounds are exemplified by sodium benzoate, parabens and derivatives, sorbic acid and its salts, propionic acids and its salts, sulfur dioxide and sulfites, acetic acid and acetates, nitrites and nitrates.

Buffering agents include acidulants and alkalizing agents exemplified by citric acid, fumaric acid, lactic acid, tartaric acid, malic acid, as well as sodium citrate, sodium bicarbonate and carbonate, sodium or potassium phosphate and magnesium oxide.

Stabilizers can include anti-oxidants, chelating agents, and enzyme inhibitors as exemplified by ascorbic acid, vitamin E, butylated hyroxyanisole (BHA), butylated hydroxytoluene (BHT), propyl gallate, dilauryl thiodipropionate, thiodipropionic acid, gum guaiac, citric acid, edetic acid and its salts and glutathione.

In embodiments of the present disclosure, the percentage dry weight concentration of at least single ingredients incorporated in a film in each of the following categories may be as follows: active agents (about 0.01-about 75%), flavoring agents (about 0.1-about 10%), coloring agents (about 0.01-about 5%), water soluble inert fillers (about 0.5-about 50%), preservatives (about 0.01-about 10%), buffering agents (about 0.1-about 10%) and stabilizers (about 0.01-about 5%).

A further optional ingredient can be an adhesion composition that is on the exterior of an embodiment of the present disclosure and, when placed in the oral cavity in contact with the mucosa therein, adheres to the mucosa. The adhesion composition can be a powder matrix and can be adjusted to vary the length of time that the film adheres to the mucosa or to vary the adhesive forces generated between the film and mucosa. The adhesion compositions adhere to the oral mucosa or to mucosa or tissue in other parts of the body, including the mouth, nose, eyes, vagina, and rectum. Examples of adhesion compositions include carboxymethycellulose, polyvinyl alcohol, polyvinyl pyrrolidone (povidone), sodiumalginate, methyl cellulose, hydroxyl propyl cellulose, hydroxypropylmethyl cellulose, polyethylene glycols, carbopol, polycarbophil, carboxyvinyl copolymers, propylene glycol alginate, alginic acid, methyl methacrylate copolymers, tragacanth gum, guar gum, karaya gum, ethylene vinyl cetate, dimenthylpolysiloxanes, polyoxyalkylene block copolymers, and hydroxyethylmethacrylate copolymers. All examples of composition provided herein are given without limiting the use or inclusion of other comparable or functionally equivalent compositions even though such comparable or functionally equivalent compositions are not listed.

Another optional ingredient can be a saliva stimulant. Exemplary saliva stimulants include, but are not limited to, acidic compounds as citric acid, malic acid, lactic acid, ascorbic acid and tartaric acid. In other embodiments, some sweeteners can be used as saliva stimulants, including but not limited to glucose, fructose, xylose, maltose, and lactose. In certain embodiments, a saliva stimulant (e.g., citric acid) can be in an amount of from about 0.1 wt % to about 10 wt %, 0.1 wt % to about 7%, 0.1% to about 6% or about 2% to about 6%. A unit dose of a saliva stimulant (e.g., citric acid) can be in an amount of from about 10 mg. to about 70 mg. A saliva stimulant may activate the salivary gland, replenish the salivary flow and, thereby, to promote a faster disintegration of the embodiments of the present disclosure and increase the speed with which the contents thereof are administered.

Embodiments of the present disclosure may be delivered for local or systemic administration to an oral cavity surface, for example, an oral mucous membrane or cheek tissue in the oral cavity, in active agent-transmitting relation thereto, the active agents being cannabinoid, for example, phytocannabinoid, caffeine, vitamins and menthol.

Embodiments of the present disclosure may be formulated to be immediate and/or modified release. Modified release formulations include delayed-, sustained-, pulsed-, controlled, targeted and programmed release.

Suitable modified release formulations for the purposes of the present disclosure may be adapted, for example, from those described in U.S. Pat. No. 6,106,864. Details of other suitable release technologies such as, for example, high energy dispersions and osmotic and coated particles are to be found in Pharmaceutical Technology On-line, 25(2), 1-14, by Verma et al (2001). The use of chewing gum to achieve controlled release may be adapted from those described in WO 00/35298.

Other embodiments of the present disclosure include a method of relieving local and/or systemic pain and/or inflammation as well as providing a stimulant and optionally providing nutrition (e.g., vitamins) by administering to the oral cavity of a mammal (e.g., human person, animal, etc. in need of such treatment) in need of such treatment at least one of the compositions disclosed herein. Still other embodiments of the present disclosure include a method of relieving mouth, oral or dental pain and/or inflammation as well as providing a stimulant and providing nutrition (e.g., vitamins) by topically administering to the oral cavity of a mammal (e.g., human person, animal, etc.) in need of such treatment at least one of the compositions disclosed herein. Still other embodiments of the present disclosure include a method of relieving pain and/or inflammation as well as providing a stimulant and providing nutrition (e.g., vitamins) by administering to the oral cavity of a mammal (e.g., human person, animal, etc.) in need of such treatment at least one of the compositions disclosed herein to a tooth, teeth or other oral tissues or surfaces. Still other embodiments of the present disclosure include a method of relieving mouth, oral or dental pain and/or inflammation as well as providing a stimulant and providing nutrition (e.g., vitamins) by topically administering to the oral cavity of a mammal (e.g., human person, animal, etc.) in need of such treatment at least one of the compositions disclosed herein to a tooth, teeth or other oral tissues or surfaces. Such methods by providing a stimulant include stimulating the brain and central nervous system and other effects of a stimulant (e.g., caffeine).

The dosing time for embodiments of the present disclosure to dissolve can range from about 5 seconds to about 60 seconds, 5 seconds to about 30 seconds, 5 seconds to about 10 seconds. If there is a remainder of an embodiment of the present disclosure that remains in the oral cavity after the above dosing times, it can then be removed from the oral cavity or chewed and swallowed to pass through the digestive system for removal.

The amount of the active agent administered (e.g., cannabinoid, menthol, stimulant, etc.) will be dependent on the subject being treated, the severity of the disorder or condition, the rate of administration, the disposition of the compound and the discretion of the prescribing physician. However, an effective dosage is in the range of about 0.001 to about 100 mg. per kg body weight per day, preferably about 1 to about 35 mg./kg/day, in single or divided doses. For a 70 kg human, this would amount to about 0.05 to about 7 g/day, preferably about 0.1 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

As used herein, the term "combination therapy" refers to the administration of an active agent together with an at least one additional pharmaceutical or medicinal agent, either sequentially or simultaneously.

The present disclosure includes the use of a combination of an active agent and one or more additional pharmaceutically active agent(s). If a combination of active agents is administered, then they may be administered sequentially or simultaneously, in separate dosage forms or combined in a single dosage form. Accordingly, the present disclosure also includes pharmaceutical compositions comprising an amount of: (a) a first agent comprising an active agent or a pharmaceutically acceptable salt of the compound; (b) a second pharmaceutically active agent; and (c) a pharmaceutically acceptable carrier, vehicle or diluent.

The compositions of the present disclosure may also serve to deliver an active agent using other routes of administration. For example, the compositions may be formulated with excipients, carriers and the like suitable for oral administration of an orally active drug.

Example 1

Low Version

Size of unit dose patch: 1 cm×1.5 cm (1.5 cm$^2$), total weight 107.44 mg. Ingredients: menthol 0.15 wt % (16 mg); caffeine 9.31 wt % (10.0 mg.); full spectrum hemp oil 1.87 wt % (2.0 mg.); vitamin B2 as ribofavin 5'-phosphate 4.65 wt % (5.0 mg.); vitamin B3 as niacinide 46.53 wt % (50.0 mg.); vitamin B5 as calcium-pantothenate 4.65 wt % (5.0 mg.); vitamin B6 as pryidoxyl 5' phosphate 2.32 wt % (2.5 mg.); vitamin B7 as biotin D 0.028 wt % (30.0 mg.); and strip material (glycerin, algin, pullulan, propylene glycol, corn starch, flavorings (peppermint oil, spearmint), coloring (tartrazine), sweetener (sucrose) and polysorbate 80) 30.49 wt % (32.75 mg.).

Example 2

Standard Version

Size of unit dose patch: 1 cm×3.3 cm (3.3 cm$^2$), total weight 1132.8 mg. Ingredients: menthol 16.84 wt % (190.8 mg); caffeine 26.49 wt % (300 mg.); full spectrum hemp oil 2.65 wt % (30 mg.); vitamin B2 as ribofavin 5'-phosphate 26.49 wt % (300 mg.); vitamin B3 as niacinide 8.82 wt % (100.0 mg.); vitamin B5 as calcium-pantothenate 1.77 wt % (20.0 mg.); vitamin B6 as pryidoxyl 5' phosphate 4.41 wt % (50 mg.); vitamin B7 as biotin D 0.88 wt % (10.0 mg.); and strip material (glycerin, algin, pullulan, propylene glycol, corn starch, flavorings (peppermint oil, spearmint), coloring (tartrazine), sweetener (sucrose) and polysorbate 80) 30.49 wt % (32.75 mg.).

Example 3

High Version

Size of unit dose patch: 1.25 cm×4 cm (5 cm$^2$), total weight 1716 mg. Ingredients: menthol 16.61 wt % (285 mg); caffeine 26.22 wt % (45.0 mg.); full spectrum hemp oil 2.62 wt % (45 mg.); vitamin B2 as ribofavin 5'-phosphate 17.48 wt % (300 mg.); vitamin B3 as niacinide 5.83 wt % (100 mg.); vitamin B5 as calcium-pantothenate 1.17 wt % (20 mg.); vitamin B6 as pryidoxyl 5' phosphate 2.91 wt % (50 mg.); vitamin B7 as biotin D 0.58 wt % (10.0 mg.); and strip material (glycerin, algin, pullulan, propylene glycol, corn starch, flavorings (peppermint oil, spearmint), coloring (tartrazine), sweetener (sucrose) and polysorbate 80) 30.49 wt % (32.75 mg.).

All publications, including but not limited to, issued patents, patent applications, and journal articles, cited in this application are each herein incorporated by reference in their entirety.

Thus, while there have been shown, described and pointed out, fundamental novel features of the present disclosure as applied to the exemplary embodiments thereof, it will be understood that various omissions and substitutions and changes in the form and details of devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

This written description uses examples as part of the disclosure, including the best mode, and also to enable any person skilled in the art to practice the disclosed implementations, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

While there have been shown, described and pointed out, fundamental features of the present disclosure as applied to the exemplary embodiments thereof, it will be understood that various omissions and substitutions and changes in the form and details of compositions, devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

The invention claimed is:

1. A dissolvable thin oral tape, film or strip or segment thereof, comprising:
   a film former;
   at least one cannabinoid includes full spectrum hemp oil and less than 0.3 wt % THC and is in an amount of from about 0.1 wt % to about 10 wt %;
   menthol is in an amount of from about 0.1 wt % to about 20 wt % in a unit dose amount of from about 0.1 mg. to about 300 mg;
   caffeine in an amount of from about 0.1 wt % to about 30 wt %; and
   vitamins in an amount of from about 0.01 wt % to about 30 wt %,
   wherein the percentage amounts are all based on the total weight of the dissolvable thin oral tape, film or strip or segment thereof and wherein the full spectrum hemp oil is purified to include the below stated amounts of one or more of the following impurities: less than 0.1 μg/kg of each of Aflatoxins BI, 82, G1, G2 and the sum of all positive Aflatoxins is less than 0.4 μg/kg; less than 0.1 mg/kg of each of Glufosinate, Glyphosate and Aminomethylphosphonic acid (AMPA); less than 0.02 mg/kg of mercury; less than 0.03 mg/kg of arsenic; less than 0.01 mg/kg of cadmium; and less than 0.05 mg/kg of lead.

2. The dissolvable thin oral tape, film or strip or segment thereof of claim 1, wherein the vitamins include B2, B3, B5, B6 and B7.

3. The dissolvable thin oral tape, film or strip or segment thereof of claim 1, wherein the at least one cannabinoid includes full spectrum hemp oil.

4. The dissolvable thin oral tape, film or strip or segment thereof of claim 1, further including at least one of a coloring agent, a flavoring, a salivary stimulating agent and a sweetening agent.

5. The dissolvable thin oral tape, film or strip or segment thereof of claim 4, wherein the salivary stimulating agent is citric acid in an amount of from about 0.1 wt % to about 10 wt %.

6. The dissolvable thin oral tape, film or strip or segment thereof of claim 1, wherein the composition is a unit dose formulation and the at least one cannabinoid includes full spectrum hemp oil in a unit dose amount of from about 2 mg. to about 45 mg.

7. A dissolvable thin oral tape, film or strip or segment thereof, comprising:
   a film former including at least one of algin and pullulan;
   a plasticizer including glycerin;
   an emulsifier including polysorbate 80;
   full spectrum hemp oil in an amount of from about 0.1 wt % to about 10 wt %;
   menthol is in an amount of from about 0.1 wt % to about 20 wt % in a unit dose amount of from about 0.1 mg. to about 300 mg;
   caffeine in an amount of from about 0.1 wt % to about 30 wt %; and
   vitamins in an amount of from about 0.01 wt % to about 30 wt % and includes vitamins B2, B3, B5, B6 and B7,
   wherein the percentage amounts are all based on the total weight of the dissolvable thin oral tape, film or strip or segment thereof and wherein the full spectrum hemp oil is purified to include the below stated amounts of one or more of the following impurities: less than 0.1 μg/kg of each of Aflatoxins BI, 82, G1, G2 and the sum of all positive Aflatoxins is less than 0.4 μg/kg; less than 0.1 mg/kg of each of Glufosinate, Glyphosate and Aminomethylphosphonic acid (AMPA); less than 0.02 mg/kg of mercury; less than 0.03 mg/kg of arsenic; less than 0.01 mg/kg of cadmium; and less than 0.05 mg/kg of lead.

8. The dissolvable thin oral tape, film or strip or segment thereof of claim 7, wherein the full spectrum hemp oil includes less than 0.3 wt % THC.

9. The dissolvable thin oral tape, film or strip or segment thereof of claim 7, wherein the vitamin B2 is riboflavin 5'-phosphate in an amount of from about 1 wt % to about 30 wt %, B3 is niacinide in an amount of from about 5 wt % to about 30 wt %, B5 is calcium-pantothenate in an amount of from about 1 wt % to about 5 wt %, B6 is pryidoxyl 5' phosphate in an amount of from about 1 wt % to about 5 wt % and B7 is biotin D is in an amount of from about 0.01 wt % to about 1 wt %.

10. The dissolvable thin oral tape, film or strip or segment thereof of claim 7, further including at least one of a coloring agent, a flavoring, a salivary stimulating agent and a sweetening agent.

11. The dissolvable thin oral tape, film or strip or segment thereof of claim 10, wherein the salivary stimulating agent is citric acid in an amount of from about 0.1 wt % to about 10 wt %.

12. The dissolvable thin oral tape, film or strip or segment thereof of claim 7, wherein the composition is a unit dose formulation and the full spectrum hemp oil in the unit dose is in the amount of from about 2 mg. to about 45 mg.

13. A method of treating pain of a mammal and stimulating the brain and central nervous system of the mammal using a therapeutic unit dose patch composition for delivery of full spectrum hemp oil, menthol, vitamins and caffeine through an oral mucous membrane of an oral cavity of the mammal, the therapeutic unit dose patch composition comprising a dissolvable thin oral tape, film or strip or segment thereof, the dissolvable thin oral tape, film or strip or segment thereof, including:
   a film former including at least one of algin and pullulan;
   a plasticizer including glycerin;
   an emulsifier including polysorbate 80;
   full spectrum hemp oil in an amount of from about 0.1 wt % to about 10 wt %;
   menthol is in an amount of from about 0.1 wt % to about 20 wt % in a unit dose amount of from about 0.1 mg. to about 300 mg;
   caffeine in an amount of from about 0.1 wt % to about 30 wt %;
   vitamins in an amount of from about 0.01 wt % to about 30 wt % and includes vitamins B2, B3, B5, B6 and B7; and a salivary stimulating agent comprising citric acid in an amount of from about 0.1 wt % to about 10 wt % in a unit dose amount of from about 10 mg. to about 70 mg., wherein the percentage amounts are all based on the total weight of the therapeutic unit dose patch composition and, wherein the full spectrum hemp oil is purified to include the below stated amounts of one or more of the following impurities: less than 0.1 μg/kg of each of Aflatoxins BI, 82, G1, G2 and the sum of all positive Aflatoxins is less than 0.4 μg/kg; less than 0.1 mg/kg of each of Glufosinate, Glyphosate and Aminomethylphosphonic acid (AMPA); less than 0.02 mg/kg of mercury;

less than 0.03 mg/kg of arsenic; less than 0.01 mg/kg of cadmium; and less than 0.05 mg/kg of lead, the method comprising:

orally administering the therapeutic unit dose patch composition to an oral cavity of the mammal to deliver the full spectrum hemp oil, menthol, vitamins and caffeine through the oral mucous membrane of the oral cavity;

leaving the therapeutic unit dose patch composition in the oral cavity for delivery of the full spectrum hemp oil, menthol, vitamins and caffeine through the oral mucous membrane of the mammal; and increasing the speed with which the full spectrum hemp oil, menthol, vitamins and caffeine are delivered through the oral mucous membrane of the mammal by stimulating the activity of a salivary gland using the citric acid to produce saliva and replenish salivary flow.

14. The method of claim 13, wherein the full spectrum hemp oil includes less than 0.3 wt % THC.

15. The method of claim 13, wherein the vitamin B2 is riboflavin 5'-phosphate in an amount of from about 1 wt % to about 30 wt %, B3 is niacinide in an amount of from about 5 wt % to about 30 wt %, B5 is calcium-pantothenate in an amount of from about 1 wt % to about 5 wt %, B6 is pryidoxyl 5' phosphate in an amount of from about 1 wt % to about 5 wt % and B7 is biotin D in an amount of from about 0.01 wt % to about 1 wt %.

16. The method of claim 13, wherein the therapeutic composition further includes at least one of a coloring agent, a flavoring and a sweetening agent.

17. The method of claim 13, wherein the therapeutic composition is a unit dose formulation and the full spectrum hemp oil in a unit dose amount of from about 2 mg. to about 45 mg.

18. The method of claim 13, wherein the pain is oral or dental pain.

* * * * *